United States Patent [19]

Pieters et al.

[11] 4,113,655
[45] Sep. 12, 1978

[54] CATALYST OF CHLORINATION AND COMBINED CHLORINATION/FLUORINATION BASED ON COPPER/CALCIUM/FLUORIDE

[75] Inventors: Wim J. M. Pieters, Morristown; Emery J. Carlson, Chatham, both of N.J.

[73] Assignee: Allied Chemical Corporation, Morris Township, Morris County, N.J.

[21] Appl. No.: 791,767

[22] Filed: Apr. 28, 1977

Related U.S. Application Data

[62] Division of Ser. No. 683,995, May 6, 1976, Pat. No. 4,039,596.

[51] Int. Cl.$^2$ .................. B01J 27/24; B01J 27/12
[52] U.S. Cl. .................................. 252/438; 252/441
[58] Field of Search ............................ 252/441, 438

[56] References Cited

U.S. PATENT DOCUMENTS

| | | | |
|---|---|---|---|
| 1,216,933 | 2/1917 | Bosch et al. | 252/441 |
| 1,681,751 | 8/1928 | Storch | 252/441 X |
| 2,154,527 | 4/1939 | Pier et al. | 252/441 X |
| 2,578,913 | 12/1951 | Whitman | 260/653.8 |
| 2,636,864 | 4/1953 | Pye et al. | 252/441 |
| 2,739,989 | 3/1956 | Barrijen et al. | 252/441 X |
| 2,784,236 | 3/1957 | Spector et al. | 252/441 X |
| 3,591,646 | 7/1971 | Vecchio et al. | 260/653.6 |

*Primary Examiner*—Delbert E. Gantz
*Assistant Examiner*—William G. Wright
*Attorney, Agent, or Firm*—Robert A. Harman

[57] ABSTRACT

The catalyst consists essentially of a calcium fluoride matrix and a thermally stable copper-containing phase as produced by coprecipitation of calcium fluoride and copper fluoride and/or calcium hydroxide and copper oxide, in presence of alkali metal or ammonium ion. The coprecipitate is thoroughly dried and heated at elevated temperature; followed, if the coprecipitate is in the form of hydroxide and/or oxide, by conversion of such hydroxide and oxide to fluoride.

The preferred alkali metal ion is potassium.

The most active and stable catalysts show by X-ray diffraction a pattern including lines characteristic of calcium fluoride and additional lines indicative of a face-centered cubic unit cell having unit dimension of about 8.1–8.4 A.

The catalyst operates at about 200°–550° C. depending to some extent on the substrate.

6 Claims, No Drawings

CATALYST OF CHLORINATION AND COMBINED CHLORINATION/FLUORINATION BASED ON COPPER/CALCIUM/FLUORIDE

This is a division of application Ser. No. 683,995, filed May 6, 1976 now U.S. Pat. No. 4,039,596.

BACKGROUND OF THE INVENTION

It is known to produce elemental chlorine by the reaction of gaseous hydrogen chloride with elemental oxygen, the so-called Deacon reaction. Moreover, such process can be combined with a process of chlorination wherein gaseous HCl and elemental oxygen are passed in vapor phase in contact with organic material to be chlorinated, under conditions such that the hydrogen chloride is oxidized with production of elemental or nascent chlorine which functions as a chlorinating agent. Such process is known as "oxyhydrochlorination," or "OHC."

The consumption of chlorine in the OHC process promotes oxidation of further quantities of the hydrogen chloride reactant. Representative of the earlier art in this area is an article in the publication, *The Chemical Engineer*, for July–August 1963 at pages 224–232 by J. T. Quant et al. A catalyst is used in such processes, especially copper chloride upon a carrier, usually a silicious carrier. Usually the catalyst is promoted by another metal chloride, especially alkali metal chloride, and/or rare earth metal chloride. For chlorination of alkanes and chloralkanes, the temperature range employed is broadly from 350° to 550° C.; and for alkenes the broad temperature range is 200° to 350° C. Ordinarily, the elemental oxygen is supplied as oxygen of air, although the process is operative with more concentrated forms of elemental oxygen. Pressures used are generally about atmospheric, but can be higher, e.g. up to 10 atmospheres.

In a modification of the "OHC" process just mentioned, fluorination can be effected upon a substance containing CCl groups, susceptible of fluorination by action of hydrogen fluoride and elemental oxygen. A variant is to expose a substance containing CH groups—susceptible of chlorination by elemental chlorine—to gaseous HCl and elemental oxygen under conditions suitable for producing chlorine; and to include hydrogen fluoride in the vapor phase to react with the chlorinated organic material thus formed. Such process is known as "oxyhydrochlorofluorination," or "OCF."

A representative disclosure of an OCF process is in British Pat. No. 745,818 of Mar. 7, 1956 to National Smelting Company Limited. In that patent the catalyst is aluminum fluoride impregnated with cupric chloride. Whitman U.S. Pat. No. 2,578,913 of Dec. 18, 1951 relates to oxidative fluorination of hydrocarbons by action of oxygen and hydrogen fluoride, using in most examples a catalyst of copper oxide supported on alumina; and disclosing also (column 5, lines 23-35) use of oxides or salts of metals such as copper, lead, chromium, and iron group metals supported on alumina, calcium fluoride, or copper gauze; also copper chromite.

Problems which have been encountered in employing such processes commercially arise from the fact that the copper chloride has enough vapor pressure at the required temperatures so that it migrates by sublimation, being carried downstream from its original position on the support. If in order to reduce the temperature required for reaction, the copper chloride is admixed with promoter salts such as potassium chloride, lithium chloride, rare earth metal chlorides and the like, eutectic compositions are formed which melt at the reaction temperatures generally required for these processes. To the extent that these volatilize and are redeposited downstream in solid form, they tend to block off passageways through the catalyst. Consequently the known catalysts for OHC and OCF reactions usually show markedly decreasing catalytic effectiveness with continuing use. Moreover, when the supported melt phase catalysts are used in particle form, as in fluid beds, the fusible constituents tend to cause catalyst agglomeration. Furthermore, the volatile and molten compounds, at the reaction temperatures, are highly corrosive even toward corrosion resistant construction material such as nickel-chromium alloys.

Attempts have been made to minimize these problems by obtaining more active catalysts, which would operate at lower temperatures than usually required; or by obtaining the copper catalyst in a stabilized active form, sufficiently stable at the reaction temperatures to avoid sublimation and melting during use. These prior efforts have not been sufficiently successful, at least with alkane substrates, to allow the general commercialization of such processes under existing economic conditions.

SUMMARY OF THE INVENTION

The present invention is directed to a new catalyst especially useful for chlorination (OHC) and chlorination-fluorination (OCF) reactions of organic compounds; to the preparation of the new catalyst; and to processes involving chloride formation from HCl and elemental oxygen, carried out in presence of the new catalyst. The catalyst is notable for being solid and nonvolatile at elevated temperatures at which it is used, having good activity and selectivity for chlorination vs. destructive oxidation of organic materials at these temperatures, being noncorrosive or only relatively slightly corrosive to metal such as nickel-chromium alloys at the temperatures of use, and being hard and resistant to abrasion and nonagglomerating.

Our catalysts are believed to consist essentially of a calcium fluoride matrix and a thermally stable copper-containing phase, which is believed to be the desired catalyst material, and to contain copper ion, calcium ion, and alkali metal or ammonium ion in combination with fluoride ion. For convenience this phase is hereinafter called the "A phase."

The most consistently good results have been obtained in our tests using catalysts containing potassium as the alkali metal ion.

Usually a copper oxide phase is also present, which may have some catalytic activity e.g., upon conversion under OHC or OCF conditions to copper chloride. Likewise, the simplest salt, $CuF_2$, is converted under reaction conditions to copper chloride. The copper chlorides as above noted are volatile; and mixtures or complexes with alkali metal chlorides form a melt phase under OHC and OCF conditions. These thermally unstable copper compounds (copper oxide, copper chlorides and copper fluorides) are undesirable in our catalysts and are minimized therein by washing them out to the extent feasible. Nonetheless, some copper oxide will remain present in interstitial positions in the calcium fluoride matrix, inaccessible to the solvent.

Typically our catalysts have a Debye-Scherrer X-ray diffraction pattern made up of the known lines for calcium fluoride and for copper oxide; together with characteristic lines produced by the A phase, having the following Bragg spacings (Angstroms) and relative intensities ($I/I_1$), where I is the intensity, normalized to 100, of the strongest line:

| Bragg Spacing (A units) | Relative Intensity |
|---|---|
| 4.68 | 100 |
| 2.87 | 70 |
| 2.44 | 17* |
| 2.34 | 50 |
| 2.03 | 55 |
| 1.66 | 21* |
| 1.56 | 18* |
| 1.44 | 23* |

These lines are near the limit of detection, so that their existence is questionable The above tabulated lines indicate that the A phase has a face-centered cubic unit cell, in which the unit dimension, $a_o$, has a value of usually 8.1–8.2 A. In some samples, values up to 8.33 A have been found.

A content of A phase, sufficient to enhance the activity of the catalyst over that of a $CaF_2/CuO$ combination as such, is near the low limit of detection by X-ray, probably as low as 5 weight percent of the catalyst. Preferred catalysts contain at least about 8 weight percent of this A phase.

As indicative of the thermal stability of our catalysts, no endotherm is observed by differential thermal analysis thereof up to a temperature of about 725° C.; and the measured content of the A phase is essentially unchanged after heating for 24 hours at 600° C. (but is diminished upon heating at 700° C.). Our catalysts are accordingly melt-free under reaction conditions. These melt-free catalysts are found to be stable against reaction of the fluoride-containing support with $CCl_4$ (to form $CCl_3F$ and $CCl_2F_2$) as occurs when a molten phase is supported on $CaF_2$. Such reaction leads eventually to consolidation and collapse of the support to a solid mass.

Oxyhydrochlorination processes using our catalyst can be performed, in general, on any organic material which contains a CH group susceptible to attack by chlorine. In particular our process is applicable to gaseous organic compounds such as methane, ethane, propane, butane and ethylene; and low-boiling partially chlorinated compounds derived therefrom. Vaporizable organic compounds such as benzene can be chlorinated by our process. Like materials are susceptible to a combined oxyhydrochlorination/fluorination process, utilizing our catalyst. Temperatures to be used are broadly 200° to 550° C., depending to some extent on the material being treated, especially about 250° to 475° C.

Referring now more particularly to the method of preparation of our catalysts, a catalyst having improved stability over those of the prior art can be prepared from oxides or hydroxides of calcium and copper precipitated, together, from an aqueous solution in the presence of a source of alkali metal or ammonium ion, especially potassium ion; then after washing, drying and heating procedures, exposed at elevated temperature to hydrogen fluoride.

Alternatively and preferably (because of their excellent activity and stability) our catalyst can be prepared by precipitating, together, calcium fluoride and copper fluoride from aqueous solution, in presence of a source of alkali metal or ammonium ion, especially potassium ion; then filtering, washing and drying the precipitate; and heating the product.

Such preferred catalysts can be obtained by precipitating, together, calcium and copper fluorides from an aqueous solution of salts thereof such as chlorides, by combining such solution with an aqueous solution of potassium fluoride, e.g., at room temperature; filtering, washing with water and drying the precipitate; heating the product for several hours at temperature of at least about 400° C. but not above about 700° C.; and washing with organic solvent to remove, as far as practical, thermally unstable copper-containing material, e.g. copper chlorides and copper oxides, and any other materials present other than the calcium fluoride matrix and the A phase.

The required coprecipitation is advisably accomplished by maintaining excess fluoride present, as by adding aqueous solution of calcium and copper chlorides to excess aqueous potassium fluoride solution.

Suitable organic solvents for washing the heat-treated coprecipitate are acetonitrile (solvent of cuprous compounds) and methanol (solvent of cupric compounds). Slight acidification (HCl) of the acetonitrile is desirable to increase uptake of cuprous chloride and the oxides therein.

The above preparative methods can be combined, e.g., by using enough KOH in aqueous solution to precipitate the copper as oxide and at least enough KF to precipitate the calcium as calcium fluoride.

DESCRIPTION OF PREFERRED EMBODIMENTS

The lettered examples below are illustrative of procedures for preparation of our catalysts. (Letter "I" is omitted to avoid confusion with Roman numeral I.)

Example A

A solution was prepared by dissolving 220.5 grams of reagent grade $CaCl_2 \cdot 2H_2O$ (1.5 mols) and 67.2 grams reagent grade $CuCl_2$ (0.5 mol) in one liter of deionized water. A second solution was prepared by dissolving 406.7 grams of reagent grade anhydrous KF (7 mols) in one liter of deionized water. The second solution was added to the first solution at room temperature with stirring. A precipitate formed. The slurry was allowed to stand overnight. The slurry was filtered on a suction funnel and washed with water, finally with distilled water (2 liters).

The filter cake was dried at 150° C. for about 66 hours, and then heated for 16 hours at 500° C. The hard material was crushed to pass through a 10 mesh screen (i.e. openings of 2 mm. × 2 mm.). The material was given a series of organic solvent washes, first with acetonitrile containing a minor amount of HCl, next with acetonitrile, and finally with methanol. (The purpose was to remove any copper chlorides). The material was then redried.

Prior to its testing and evaluation as a catalyst, the material was again crushed to pass through No. 80 mesh screen (i.e. openings of 0.177 mm. × 0.177 mm.).

The catalyst of this Example A had surface area (measured by the BET method using nitrogen gas) of about 4–5 sq. meters per gram. It is hard and resistant to mechanical disintegration; hence, can be used in a fluidized bed. The catalyst analyzed about 14% copper and 6% potassium. It showed presence of "A" phase by X-ray.

The catalyst was tested for corrosiveness upon heating in a nickel/chromium alloy (INCONEL) reactor and was found to cause little or no corrosion at temperatures of 425° C. over a test period of 200 hours in nitrogen, then 300 hours under OCF conditions, then 50 hours under OHC conditions. The catalyst still retained much of its activity after this test had been concluded.

Example B

In an alternative procedure, copper oxide and calcium hydroxide were precipitated from aqueous solution of the chlorides in various ratios of weight percents from 5/95 to 40/60 calculated as CuO/CaO, proceeding as follows. Anhydrous $CuCl_2$ and $CaCl_2·2H_2O$ were dissolved and brought to about 75°–85° C. in about 3 liters of water, in amounts ranging from 8.45 gm. $CuCl_2$/249.1 gm. $CaCl_2·2H_2O$ to 67.6 gm. $CuCl_2$/157.3 gm. $CaCl_2·2H_2O$, calculated to produce the desired weight ratios of the oxides. Then the amount of KOH, dissolved in about 1 liter of water, theoretically required to form cupric oxide monohydrate and calcium hydroxide was added at 75°–85° C. over about 0.5 hour followed by stirring for about 1 hour. The precipitate was allowed to settle, was filtered and was washed with at least 4 liters of water. The precipitate was dried in a 150° C. oven overnight; then was further heated in a 300° C. oven overnight. The material was crushed and screened to pass through 10 mesh and be retained on 50 mesh.

The surface areas of the resulting products were from about 15 to about 40 sq. meters per gram in various preparations.

Conversion to fluorides was effected, for example, as follows. About 50 ml. of the copper oxide/calcium hydroxide product of 20/80 weight ratio of CuO/CaO was exposed to a flow of HF gas (50cc./min.) diluted with dry nitrogen gas (150 cc./min.) in a nickel-copper alloy (MONEL metal) reactor of about ¾ inch diameter, placed in horizontal position and heated by a surrounding electrically heated furnace, temperature controlled by thermostat. The gas mixture of HF and dry $N_2$ was passed through the reactor at temperatures increasing stepwise from 250° to 450° C. The temperature was not allowed to exceed 250° C. for the first 65 hours. After 97 hours, HF flow was stopped, and the material was purged with dry nitrogen at a furnace temperature of 300° C. The material was finally vacuum dried overnight at 125° C. That portion used for catalytic evaluation was further reduced in size to minus 40 mesh screen size (i.e. to pass through openings of 0.42 × 0.42 mm.)

The surface area of the resulting material was about 5 to 6 sq. meters per gram.

A sample of a catalyst, prepared by precipitation (at 20/80 weight ratio CuO/CaO) from cupric chloride and calcium chloride using KOH followed by exposure to HF, essentially as above described, was tested for any evidence of volatility by thermogravimetric analysis ("TGA"). About 6% of its weight was lost in 3 hours of heating the dried preparation at 500° C.; and no further loss occurred on heating up to and holding at about 600° C. for another 25 hours. On the other hand, a conventional oxyhydrochlorination catalyst consisting essentially of molten $CuCl_2KCl$ supported on silica showed, on similar testing, continuing loss of weight at 500° C. amounting to about 11% at 3 hours and 18% at 15 hours.

In a comparison by differential thermal analysis ("DTA"), a sample of the subject catalyst showed no phase transition until about 850° C., i.e., it was completely thermally stable to at least 800° C.; whereas the conventional oxyhydrochlorination catalyst above cited showed an endotherm at 360° C. indicative of a phase change, i.e., some thermal instability at that temperature.

EXAMPLE C

A catalyst was prepared by precipitating copper and calcium fluorides from an aqueous solution of the chlorides using aqueous KF, generally as in Example A above, but in presence of fine particles of silica. The silica was later removed by exposure at elevated temperature to HF, whereby to increase the catalyst porosity and surface area. No washing with organic solvents was employed.

Specifically, 44.81 grams (⅓ mol) of reagent grade $CuCl_2$ and 147.0 grams (1 mol) of $CaCl_2·2H_2O$ were dissolved in 400 ml. of deionized water to which 6 grams of colloidal pyrogenic silica pigment (CAB-O-SIL) was added with stirring, forming a slurry. A solution of 232 grams of KF in 600 ml. of water was added with stirring. After 1 hour standing the solids were filtered off and water washed; then dried at 150° C. overnight. The product was heated overnight at 400° C.

About 50 ml. of this product was exposed to a flow of HF (50 cc./min.) diluted with dry nitrogen (150 cc./min.) at temperature held at about 450° C. for about 1 day.

The surface area of the preparation including the silica ingredient was about 6.50 sq. meters per gram; and that for the fluoride catalyst after removal of the silica was about 4.5 sq. meters per gram.

Catalyst Evaluations in OHC

The catalysts prepared in Examples A, B and C were tested in oxyhydrochlorination runs with methane. The results are summarized in Table 1 below.

The reactor used consisted essentially of an open ended quartz tube, surrounded by a jacket, and supported in an electrically heated furnace. Reactant gases are supplied through inlet valves and pass out through exit valves. The valves are thermally controlled by a temperature controller. The jacket is sealed to the inner tube near the top of that tube and closes over below the open bottom end of the reactor tube.

The reactant gases enter the jacket through a side arm, flow down the annulus between the jacket and the inner tube to the closed off bottom of the jacket, rise from there into the open end of the reactor tube, pass through the catalyst bed therein, and exit from the top of the reactor tube.

The exit manifold delivers reactants to product separating chromatographic columns and associated detectors, and vent. The flows of the three principal reactant gases, HCl, $O_2$, $CH_4$ and diluent gas $N_2$ are set and regulated by electronic flow controllers. Total pressure of the combined reactant mixture is recorded by a pressure recorder ahead of the inlet.

Carrier gas helium is controlled by a pressure regulator and diverted to the chromatographic columns by another valve.

The initiation, duration and temperature-time profile for a catalyst test run are controlled by a conductive tape prgrammer, 60-hour clock and percent timer. The tape program, in turn, governs a cam programmer which controls the product gas sampling and analyses. On command from the tape programmer, the cam programmer diverts product gas stream and helium to chromatographic columns. The command also initiates the temperature regimen required for the chromatographic cycle via a Hewlett Packard 5750 chromatographic programmer. Further, the command from the cam diverts the more volatile product gases, not well resolved in the first (high temperature) chromatographic column to the second chromatographic column via a manifold. Finally, the command from the cam initiates the product gas analyzer which furnishes (using thermal conductivity detector bridge circuits) conventional peak traces via a chromatograph peak recorder.

Simultaneously, the bridge circuit emf's are transmitted to two channels of a time-sharing computer and returned as component concentrations via teletype printout. Channel No. 1 printout shows the concentrations of low boiling product cmponents reported in volume percent ($O_2$, $CH_4$, CO), and also gives the reactor temperature, the operating pressure, and a reference flow (usually the HCl flow) all at sampling time. Channel No. 2 printout shows the concentrations of the higher boiling product components- $CO_2$, HCl, $H_2O$, $CH_3Cl$, $COCl_2$, $CH_2Cl_2$, $CHCl_3$, $CCl_4$. A four-point temperature profile from thermocouples along the inside furnace wall is stored continuously by a temperature recorder. The temperature of the sampling valve manifolds is also recorded here.

Inlet concentrations of the reactants are programmed for analysis each hour, during the time while the temperature of the reactor furnace is being changed in a given series of runs over a given catalyst.

(4) Yield: 100 [CM]/ [$CH_4$]in
(5) Depth of chlorination: 25{[$CH_3Cl$] + 2[$CH_2Cl_2$] +3[$CHCl_3$] + 4[$CCl_4$]}/[CM]
(6) Overall reaction rate: Reactant flow in mols per sec. × {[$CH_4$]in − [$CH_4$]out}/ 100 × gms. of catalyst in the tube
(7) Specific reaction rate: Overall reaction rate/- Catalyst surface area in sq. meters per gm.
(8) extent of "Deacon" reaction: 100 × {[HCl]in + [HCl]formed − [HCl]out}/ [HCl]in + [HCl]formed, where [HCl]formed is that theoretically formed by reaction of $Cl_2$ with a methane hydrogen atom (forming ≡ CCl + HCl); i.e., [HCl]formed = [$CH_3Cl$] + 2[$CH_2Cl_2$] + 3[$CHCl_3$] + 4[$CCl_4$]
(9) Performance Factor" rates the performance in terms of HCl utliziation ("Deacon"), "Depth" as above defined and "Yield," by forming a ratio of each to a target value, and weighting their significance by raising to a power: "Perf. Fact." = 100 × (Deacon/90)$^3$ × (Depth/87) 2 × (Yield/80)
(10) The "Sum of Errors" indicates how closely the analysis of reactants and products approached to material balance. The procedure for determining these "Errors" is as follows.

Material balance for the chemical in the system is estimated by computer, using a linear programming technique. Stoichiometry is impressed by supplying a set of balanced chemical equations to the program. The following eight reactions which can account for all reactants and final products are available to the OHC program:

Table I

| Run No. | Temp. Deg. C. | Res. Time Sec. (1) | $CH_4$ Conversion (2) | Chlor-methane Select. (3) | Chlor-methane Yield (4) | Depth of chlor. (5) | Reaction rate × 10$^7$ Overall MOL/G-Sec. (6) | Reaction rate × 10$^7$ Specific MOL/$M_2$-Sec. (7) | Deacon based on HCL (8) | Perf fact (9) | Sum of errors (10) |
|---|---|---|---|---|---|---|---|---|---|---|---|
| Part A | | | | | | | | | | | |
| 1. | 424 | 2.38 | 100 | 69.6 | 69.6 | 93.3 | 4.9 | 0.98 | 84.3 | 82.1 | 13.9 |
| 2. | 418 | 2.40 | 98.9 | 69.2 | 68.4 | 90.2 | 4.8 | 0.96 | 80.3 | 65.2 | 14.6 |
| 3. | 413 | 2.42 | 97.7 | 71.0 | 69.4 | 86.2 | 4.6 | 0.92 | 76.0 | 51.3 | 12.9 |
| 4. | 596 | 2.48 | 83.9 | 80.5 | 67.5 | 65.6 | 3.9 | 0.78 | 60.9 | 14.8 | 9.0 |
| 5. | 389 | 2.51 | 65.2 | 85.3 | 55.6 | 51.9 | 3.1 | 0.63 | 45.9 | 3.3 | .4 |
| Part B | | | | | | | | | | | |
| 6. | 408 | 2.44 | 100 | 52.1 | 52.1 | 83.5 | 11.1 | 1.9 | 62.6 | 20.1 | 282 |
| 7. | 403 | 2.45 | 92.4 | 17.0 | 15.7 | 60.4 | 9.9 | 1.7 | 60.4 | <1 | 0.0 |
| 8. | 385 | 2.52 | 94.1 | 24.5 | 23.1 | 70.4 | 9.8 | 1.7 | 30.8 | <1 | 0.0 |
| As a variant in the catalyst preparation of this Part B, a catalyst was prepared essentially as in Example B except that the chloride solution was added to the KOH solution, instead of vice versa. A better catalyst was obtained, on the basis of the results below (Runs 9 and 10). | | | | | | | | | | | |
| 9. | 412 | 2.42 | 98.9 | 70.6 | 69.8 | 87.8 | 12.4 | 3.7 | 79.2 | 60.5 | 45.8 |
| 10. | 403 | 2.45 | 88.8 | 88.5 | 78.8 | 80.5 | 11.0 | 3.3 | 78.7 | 56.3 | 23.6 |
| The "oxide route" catalysts of this Part B are not as stable under OHC conditions as the "fluoride route" catalysts of Parts A and C. At elevated temperatures under OHC conditions there was significant production of $CFCl_3$, evidently by reaction between the "oxide route" catalysts and $CCl_4$ product; and these catalysts showed signs of disintegrating and agglomerating in use. | | | | | | | | | | | |
| Part C | | | | | | | | | | | |
| 11. | 462 | 2.26 | 93.7 | 56.9 | 53.3 | 89.6 | 6.1 | 1.5 | 72.7 | 37.2 | .9 |
| 12. | 454 | 2.28 | 99.1 | 49.3 | 48.8 | 92.3 | 6.4 | 1.6 | 69.5 | 31.7 | .1 |
| 13. | 443 | 2.32 | 98.6 | 48.4 | 47.7 | 90.5 | 6.4 | 1.6 | 68.0 | 27.8 | .0 |
| 14. | 433 | 2.35 | 96.5 | 65.6 | 63.4 | 88.6 | 6.2 | 1.5 | 80.7 | 59.4 | 3.6 |
| 15. | 424 | 2.38 | 96.1 | 71.8 | 69.0 | 86.8 | 6.3 | 1.6 | 85.3 | 72.9 | 3.8 |
| 16. | 413 | 2.42 | 87.6 | 77.7 | 68.0 | 85.9 | 5.9 | 1.5 | 86.5 | 73.5 | .9 |
| 17. | 402 | 2.46 | 60.2 | 52.1 | 31.4 | 73.2 | 3.8 | 0.9 | 45.3 | 3.5 | 4498.1 |

The headings of the table are explained as follows, where [ ] represents mols concentration per 100 mols of the inlet reactants (i.e., $CH_4$, $O_2$ and HCl) and [CM] represents total mols of chlorinated methanes per 100 mols of reactants.

(1) Residence time: (catalyst void space)/(inlet gas flow at reaction temperature)
(2) $CH_4$ conversion: 100 {[$CH_4$] in − [$CH_4$]out}/[$CH_4$]in
(3) Selectiivity: 100 [CM]/{[$CH_4$]in − [$CH_4$]out}

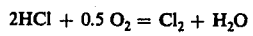

$2HCl + 0.5 O_2 = Cl_2 + H_2O$

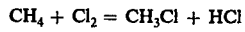

$CH_4 + Cl_2 = CH_3Cl + HCl$

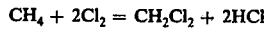

$CH_4 + 2Cl_2 = CH_2Cl_2 + 2HCl$

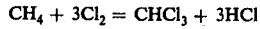

$CH_4 + 3Cl_2 = CHCl_3 + 3HCl$

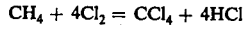

$CH_4 + 4Cl_2 = CCl_4 + 4HCl$ $$0.5O_2 + CH_4 + 3Cl_2 = COCl_2 + 4HCl$$

$$O_2 + CH_4 + 2Cl_2 = CO_2 + 4HCl$$

$$0.5O_2 + CH_4 + 2Cl_2 = CO + 4HCl$$

One function of the program is to select the extent of each (including zero) that could account for successively "less costly" estimates of the material balance, finally of the least costly. The program assigns linear program "costs", in this case incremental penalties (results of which are to be summed and minimized) for adjusting the chromatographically determined reactant and product concentrations. Costs are assigned on the basis that those associated with most precisely analyzed compounds be high, those with less precisely analyzed compounds be low. The list is given below.

| Compound Reactants | Range % | Cost per unit change | Range % | Cost per unit change |
|---|---|---|---|---|
| $O_2$ | ±10 | 50 | >10 | 5000 |
| $CH_4$ | ±10 | 50 | >10 | 1000 |
| HCl | ±15 | 1 | >15 | 1500 |
| Products |  |  |  |  |
| $O_2$ | ±10 | 50 | >10 | 1500 |
| $CH_4$ | ±10 | 50 | >10 | 3000 |
| CO | ±10 | 50 | >10 | 2000 |
| $CO_2$ | ±10 | 50 | >10 | 2000 |
| $H_2O$ | 0 | 0 | 0 | 0 |
| HCl | 0 | 0 | 0 | 0 |
| $Cl_2$ | 0 | 0 | 0 | 0 |
| $COCl_2$ | ±20 | 50 | >20 | 500 |
| $CH_3Cl$ | ±20 | 50 (30)* | >20 | 500 |
| $CH_2Cl_2$ | ±25 | 50 (20)* | >25 | 500 |
| $CHCl_3$ | ±30 | 50 (10)* | >30 | 500 |
| $CCl_4$ | ±35 | 50 (5)* | >55 | 500 |

*Note: The "cost" units are less for adjusting the various chloromethane values downward (see values in parentheses) rather than upward.

For example the penalty or cost for adjusting the oxygen concentration from the chromatographic value is 50 per unit change in oxygen concentration (if within ± 10% range); while for HCl the cost is only 1 per unit change (if within ± 15% range). Notice that the cost is greater for adjusting a concentration beyond a stated range. The program calls for no cost penalty for adjustments of the concentration of $H_2O$, HCl or chlorine in the exit stream, since these are determined only by the calculation of material balance.

The "least cost" material balance resulting from the catalyst run (at a given set of conditions) is printed. The values for each inlet component are normalized to give 100 mols total. The exit components are on the same scale. The sum of costs (i.e., the product of assigned cost change in each concentration), resulting upon adjusting the experimental concentration values to arrive at the "least cost" material balance, is printed as SUM OF ERRORS.

ANALYSES

The following is a table showing concentrations (original and corrected) obtained as described for Run 1 of the above Table I, illustrative of the detailed results obtained in the runs of the Table. The original value for [HCl]in is only a rough estimate,

ANALYSES

| Run No. | Temp. °C. |  | $O_2$ | $CH_4$ | HCl | $H_2O$ | CO | $CO_2$ | $Cl_2$ | $COCl_2$ | $CH_3Cl$ | $CH_2Cl_2$ | $CHCl_3$ | $CCl_4$ |
|---|---|---|---|---|---|---|---|---|---|---|---|---|---|---|
| 1 Original data | 424 | (In) | 29.46 | 16.13 | 54.40 | 0 | 0 | 0 | 0 | 0 | 0 | 0 | 0 | 0 |
|  |  | (Out) | 1.69 | 0 | 10.37* | 52.94* | 0 | 4.25 | 0* | 0.42 | 0 | 0.32 | 2.04 | 9.11 |
| Data corrected to obtain material balance |  | (In) | 30.17 | 15.02 | 54.40 | 0 | 0 | 0 | 0 | 0 | 0 | 0 | 0 | 0 |
|  |  | (Out) | 1.53 | 0 | 14.73 | 48.49 | 0 | 4.25 | 0 | 0.32 | 0.10 | 0.32 | 1.83 | 8.20 |

*Estimated value; not used in determining material balances because this constituent of the exit gases is partially condensed in a trap, prior to the chromatographic analysis.

For the five runs of the above Table I, Part A, the average inlet reactant concentrations and their standard deviations are shown below, as illustrative of our procedure.

|  | $O_2$ | $CH_4$ | HCl | $Cl_2$ |
|---|---|---|---|---|
| Avg. Inlet Concn.: | 29.2 | 14.5 | 56.5 | 0 |
| Standard Deviation: | 1.3 | 0.7 | 1.5 | 0 |

Example D

A catalyst was prepared as in Example A, except that the mol ratio of $CuCl_2:CaCl_2\cdot 2H_2O$ in the starting material was 1:9; the chloride solution was added to excess fluoride solution, the precipitation of fluorides was at about 90° C.; and the heating (at 500° C.) was in nitrogen gas. Results obtained in two series of OHC runs with methane are summarized under Part D (Runs 18–24) in Table II below, wherein the explanation of the headings is as for Table I; and the reactor and testing and analysis procedures used were the same as described above.

Example E

Another catalyst was prepared as just described, except that the precipitation was at room temperature. Table II below summarizes the results obtained using this catalyst in oxyhydrochlorination of methane, under Part E (Runs 25–31).

Example F

A catalyst was prepared as in Example E above except that ammonium fluoride instead of potassium fluoride was used to coprecipitate copper and calcium fluorides.

The results obtained using this catalyst are summarized in Part F (Runs 32–34) of Table II below.

Table II

| Run No. | Res. Time Sec. | Inlet | | | | Exit | | | | | |
|---|---|---|---|---|---|---|---|---|---|---|---|
|  |  | Temp. °C | $O_2$ % | $CH_4$ % | HCl % | Conv. % | Selec. % | Yield % | Depth | Deacon % | Perf. Fact |
| Part D |  |  |  |  |  |  |  |  |  |  |  |

Table II-continued

| Run No. | Inlet Res. Time Sec. | Temp. °C | $O_2$ % | $CH_4$ % | HCl % | Exit Conv. % | Selec. % | Yield % | Depth | Deacon % | Perf. Fact |
|---|---|---|---|---|---|---|---|---|---|---|---|
| 18. | 2.25 | 450 | 29.7 | 15.2 | 54.9 | 100 | 58.8 | 58.8 | | 77.8 | 58 |
| 19. | 2.30 | 426 | 29.2 | 14.5 | 55.5 | 100 | 59.6 | 59.6 | 91.6 | 73.7 | 45 |
| 20. | 2.35 | 420 | 28.9 | 14.5 | 55.9 | 96.1 | 58.6 | 56.3 | | 69.1 | 32 |
| 21. | 2.19 | 427 | 30.5 | 15.1 | 50.1 | 94.3 | 70.3 | 66.5 | 83.8 | 83.2 | 61 |
| 22. | 2.38 | 424 | 36.3 | 13.3 | 56.5 | 100 | 52.8 | 52.8 | | 100 | 113 |
| 23. | 2.43 | 410 | 37.7 | 13.2 | 55.2 | 98.6 | 56.8 | 56.0 | | 100 | 105 |
| 24. | 2.47 | 400 | 38.4 | 14.7 | 47.2 | 96.3 | 60.2 | 58.0 | 93.4 | 77 | |
| Part E | | | | | | | | | | | |
| 25. | 2.35 | 434 | 28.3 | 14.9 | 56.7 | 100 | 58.0 | 58.0 | | 72.4 | 40 |
| 26. | 2.43 | 410 | 28.4 | 14.3 | 56.7 | 99.1 | 59.9 | 59.4 | | 70.7 | 38 |
| 27. | 2.47 | 399 | 28.2 | 13.8 | 57.4 | 95.0 | 65.7 | 62.4 | | 65.3 | 24 |
| 28. | 1.73 | 423 | 35.8 | 14.0 | 55.2 | 100 | 45.1 | 45.1 | 93.1 | 100 | 88 |
| 29. | 1.79 | 400 | 37.7 | 14.3 | 53.9 | 100 | 56.9 | 56.9 | 92.5 | 100 | 110 |
| 30. | 1.81 | 392 | 39.4 | 14.6 | 46.1 | 98.0 | 61.9 | 60.5 | 84.8 | 99.3 | 96 |
| 31. | 1.85 | 380 | 40.0 | 14.8 | 45.2 | 84.0 | 65.6 | 55.0 | | 68.0 | 18 |

In Runs 22–24 and 28–31 having relatively high inlet oxygen concentrations, higher concentrations of chlorine are generated. This results in higher conversions to $CCl_4$ vs. lower chlorinated methanes. Sinces $CCl_4$ is more stable toward oxidation than the lower chlorinated methanes, higher extent of Deacon reaction is accordingly attained, and higher performance factors.

Part F

| 32. | 2.37 | 428 | 40.6 | 15.7 | 43.7 | 100 | 41.3 | 41.3 | 89.6 | 93.6 | 62 |
| 33. | 2.40 | 418 | 41.3 | 16.2 | 42.8 | 92.2 | 48.7 | 45.0 | 78.8 | 88.2 | 43 |
| 34. | 2.45 | 405 | 41.8 | 16.5 | 41.7 | 74.6 | 71.5 | 53.2 | 67.8 | 79.8 | 28 |

Catalyst Evaluations In OCF

The Examples below and the runs of Table III below show preparations and summarize tests of our catalysts in combined chlorination and fluorination ("OCF") of methane/$CCl_4$/$CCl_3F$ mixtures by oxygen/HCl/HF.

Example G

A mixed fluoride was produced from oxide precipitate of 20/80 weight ratio (calculated as CuO/CaO) as in Example B above, except that the exposure to HF/nitrogen was at about 250° C. for about 18 hours; then rising to about 375° C. in about 3 hours; maintaining 375° C. for about 16 hours; rising to 450° C. in about 1 hour; and maintaining 450° C. for about 6 more hours (a total heating period of about 50 hours).

The resulting material (volume about 27 cc.) was impregnated with anhydrous formic acid solution of KCl/LiCl in weight proportion of about 55/45 or about 1.07 gm. of KCl/0.88 gm. g. of LiCl, per 14 gms. of fluoride base (about 27 cc., of solution), overnight. The product then was heated in a 100° C. vacuum oven for about 65 hours thus removing the formic acid.

This preparation of Example G was tested as shown in Part G (Runs No. 35–38) of Table III below for OCF of methane/$CCl_4$/$CCl_3F$ mixture.

Example H

A mixed fluoride catalyst starting material was produced by coprecipitating copper and calcium fluorides as in Example A above; it was then slurried (after washing) with aqueous KCl/$LaCl_3$. The molar proportions were 1 $CuCl_2$, 4$CaCl_2$, 0.67 Kcl, 0.33 $LaCl_3$ (equivalent theoretically to composition by weight of 18.6% $CuF_2$, 57.3% $CaF_2$, 9.1% KCl, 15.0% $LaCl_3$). The slurry was dried in air at 150° C. and finally at 400° C.

Results obtained in OCF of methane/$CCl_4$/$CCl_3F$ mixture are shown in Part H (Runs 39–42) of Table III. In the table, "Res. Time" is defined as before, i.e., Res. Time = (catalyst void space)/(inlet gas flow at reaction temperature); gas concentrations (both inlet and outlet) are expressed as before, in mols per 100 mols of inlet reactants. The headings of Table III under Results are explained in the footnotes to the Table, in which [ ] indicates concentration in mols per 100 mols of inlet reactants, and [CM] indicates the sum of the concentrations of net products.

In the OCF runs, in addition to the analyses performed as above described for OHC runs, it was necessary to analyze for chlorine, HCl and HF. This was done as follows:

The effluent gas consisting of moisture, HCl, $Cl_2$, $O_2$, $CH_4$, HF and low boiling chloro-fluoro methanes, plus possible $CO_2$, CO, and input diluents was further diluted with an inert gas to prevent condensation and then bubbled through a known amount of caustic solution for a given period of time. An aliquot of the aqueous solution was analyzed for chloride ion (due to the HCl) by gravimetric precipitation as silver chloride; fluoride and hypochlorite did not interfere. Another aliqot was reduced in solution and the gravimetric determination repeated for total Cl, including that due to both HCl and $Cl_2$. As a confirmation the gas was also separately bubbled through water instead of caustic, the HCl and HF dissolving and most of the $Cl_2$ passing through; and this solution was used for the chloride ion analysis, as well as for HF values after distillation.

Table III

| Run No. | Res. Time Sec. | Temp. °C | | $O_2$ | $CH_4$ | HCl | HF | $H_2O$ | CO | $CO_2$ | $CHCl_3$ | $CCl_4$ | $CCl_3F$ | $CCl_2F_2$ |
|---|---|---|---|---|---|---|---|---|---|---|---|---|---|---|
| Part G | | | | | | | | | | | | | | |
| 35. | 1.67 | 455 | (In) | 24.9 | 11.7 | 30.9 | 18.6 | 0 | 0 | 0 | 0 | 6.9 | 6.9 | 0 |
| | | | (Out) | 3.4 | 0.4 | 6.2 | 8.1 | 39.1 | 0 | 1.9 | 2.5 | 5.6 | 12.9 | 2.3 |

In this Run 32, full analytical results are shown by way of illustration; whereas in the remaining runs of this Table only summaries are shown.

| 36. | 1.73 | 430 | | 24.9 | 11.6 | 31.0 | 18.7 | | | | | 6.9 | 6.9 | |
| 37. In | 1.78 | 410 | | 24.9 | 11.3 | 31.1 | 18.7 | | | | | 6.9 | 6.9 | |

4,113,655

Table III-continued

| | | | | | | | | |
|---|---|---|---|---|---|---|---|---|
| 38. | 1.81 | 400 | 24.8 | 11.8 | 30.9 | 18.6 | 6.9 | 6.9 |

| | | | | Results | | | |
|---|---|---|---|---|---|---|---|
| Run No. | CH4 Conv. % (1) | Yield % (2) | Deacon % (3) | HF Conv. % (4) | HF Selec. % (5) | CCl$_3$F (out) | CCl$_2$F$_2$ (out) |
| Part G | | | | | | | |
| 35. | 96.5 | 80.4 | 91.9 | 56.8 | 99.5 | 12.9 | 2.3 |
| 36. | 90.4 | 77.6 | 84.8 | 53.9 | 99.4 | 12.3 | 2.3 |
| 37. | 71.3 | 63.3 | 71.7 | 40.2 | 99.1 | 12.9 | 0.8 |
| 38. | 46.1 | 45.8 | 57.1 | 32.3 | 98.6 | 12.9 | 0.0 |

| Run No. | Res. Time Sec. | Temp. °C. | O$_2$ | CH$_4$ | HCl | HF | H$_2$O | CO | CO$_2$ | CHCl$_3$ | CCl$_4$ | CCl$_3$F | CCl$_2$F$_2$ |
|---|---|---|---|---|---|---|---|---|---|---|---|---|---|
| Part H | | | | | | | | | | | | | |
| 39. | 1.67 | 455 | 24.8 | 11.9 | 30.9 | 18.6 | | | | | | 6.8 | 6.9 |
| 40. In | 1.68 | 450 | 24.8 | 11.9 | 30.9 | 18.6 | | | | | | 6.8 | 6.9 |
| 41. | 1.73 | 430 | 25.0 | 11.1 | 1.77 | 18.7 | | | | | | 6.9 | 7.0 |
| 42. | 1.77 | 415 | 24.5 | 11.0 | 31.0 | 18.7 | | | | | | 6.8 | 7.0 |

| | | | | Results | | | |
|---|---|---|---|---|---|---|---|
| Run No. | CH4 Conv. % (1) | Yield % (2) | Deacon % (3) | HF Conv. % (4) | HF Selec. % (5) | CCl$_3$F (out) | CCl$_2$F$_2$ (out) |
| Part H | | | | | | | |
| 39. | 99.9 | 55.7 | 82.8 | 25.4 | 98.9 | 11.6 | 0.0 |
| 40. | 98.4 | 56.8 | 82.0 | 23.3 | 98.8 | 11.2 | 0.0 |
| 41. | 93.3 | 50.4 | 71.3 | 22.1 | 98.6 | 11.1 | 0.0 |
| 42. | 83.2 | 49.7 | 60.5 | 13.9 | 96.1 | 9.5 | 0.0 |

Explanations of Headings of Results
(1) CH$_4$ Conv. = $100 \times \{[CH_4]_{in} - [CH_4]_{out}\}/[CH_4]_{in}$
(2) Yield = $_{100[CM]/[CH4]_{in}} = 100 \times \{[CHCl_3]_{net} + [CCl_4]_{net} + [CCl_3F]_{net} + [CCl_2F_2]_{net}\}$, where "net" indicates [ ]$_{out}$ − [ ]$_{in}$
(3) Deacon = $_{100 \times \{[HCl]_{in} + [HCl]_{formed} - [HCl]_{out}\}/\{[HCl]_{in} + [HCl]_{formed}\}}$, where [HCl]$_{formed}$ = 3[CHCl$_3$]$_{net}$ + 4[CCl$_4$]$_{net}$ + 5[CCl$_3$F]$_{net}$ + 6[CCl$_2$F$_2$]$_{net}$
(4) HF Conv. = $_{100 \times \{[HF]_{in} - [HF]_{out}\}/[HF]_{in}}$
(5) HF Selec. = $_{100 \times \{2[CCl_2F_2]_{net} + [CCl_3F]_{net}\}/\{[HF]_{in} - [HF]_{out}\}}$

CATALYST EVALUATIONS IN OHC OF ETHYLENE

Example J

A catalyst was prepared as in Example A above, except that the mole ratio of CuCl$_2$:CaCl$_2$.2H$_2$O in the starting material was 1:9 and the final heating at 500° C. was in nitrogen atmosphere instead of air.

The volume of catalyst in the reactor was 4.5 ml. The total inlet gas flow rate into the reactor was 35 ml. of gas (at room temperature) per minute.

The results are shown in the following Table IV, wherein "VCM" signifies vinyl chloride monomer and "EDC" signifies ethylene dichloride. Compositions are given in mols per 100 mols of inlet gas. "Conv. Ethylene" is the percent of ethylene converted to products, as calculated from the analysis of the exit gas stream as compared to the ethylene analysis of the inlet gas:

Conv. Ethylene = $100 \times \{[EDC] + [VCM] + 0.5[CO]\}/[C_2H_4]_{in}$

Table IV

| Inlet Composition | | | | Temperature | Exit Composition | | | | | Conv. Ethylene |
|---|---|---|---|---|---|---|---|---|---|---|
| N$_2$ | O$_2$ | C$_2$H$_4$ | HCl | °C | O$_2$ | CO | CO$_2$ | VCM | EDC | % |
| 39.2 | 11.9 | 19.1 | 29.9 | 436 | 3.24 | .84 | 0 | 4.73 | 4.80 | 52 |
| 39.4 | 12.6 | 19.2 | 28.9 | 427 | 3.60 | .58 | 0 | 3.81 | 5.43 | 50 |
| 39.6 | 12.4 | 19.3 | 28.7 | 421 | 3.94 | 0 | 0 | 3.01 | 5.96 | 46 |
| 39.7 | 12.1 | 19.1 | 29.1 | 414 | 4.38 | 0 | 0 | 2.22 | 6.31 | 45 |

It is notable that the stability of the present catalyst allows its use in OHC of ethylene at temperatures at which a substantial proportion of the chlorinated product is vinyl chloride instead of being almost all ethylene dichloride.

We claim:

1. Catalyst effective for oxidation, by elemental oxygen, of hydrogen chloride accompanied by chlorination of organic material or by such chlorination together with fluorination with hydrogen fluoride, which catalyst consists essentially of a calcium fluoride matrix and a thermally stable phase containing copper ion, calcium ion, and alkali metal or ammonium ion in combination with fluoride ion, which phase is herein referred to to as the "A phase"; said catalyst having Debye-Scherrer X-ray diffraction pattern including lines characteristic of calcium fluoride and lines, characteristic of the A phase, having the following Bragg spacings in Angstrom units and the following relative intensities (I/I$^1$):

| Bragg spacings | Relative intensities |
|---|---|
| 4.68 | 100 |
| 2.87 | 70 |
| 2.34 | 50 |
| 2.03 | 55 | said catalyst being thermally stable to at least 600° C. upon heating for 24 hours.

2. Catalyst of claim 1 wherein the alkali metal ion present is potassium.

3. Catalyst of claim 2 wherein the A phase is at least 5 weight percent of the composition and the ratio of copper-calcium in the catalyst, expressed as calculated weight percent of CuO/CaO, is from 5/95 to 40/60.

4. Process for producing a catalyst for oxidation of hydrogen chloride by elemental oxygen, comprising precipitating, together, oxides and/or hydroxides and/or fluorides of calcium and copper from an aqueous solution in presence of alkali metal or ammonium ion; washing, drying and heating the precipitate, and if necessary to convert to fluorides, exposing the product at elevated temperature to hydrogen fluoride.

5. Process of claim 4 comprising precipitating, together, calcium fluoride and copper fluoride from aqueous solution in presence of a source of potassium ion; and washing the product of the heating step with organic solvent to remove copper chlorides.

6. Process of claim 5, wherein the heating step is at temperature of at least about 500° C. but not above about 700° C., and the resulting product is washed with solvent comprising acetonitrile and methanol.

* * * * *

UNITED STATES PATENT AND TRADEMARK OFFICE
CERTIFICATE OF CORRECTION

PATENT NO. : 4,113,655

DATED : September 12, 1978

INVENTOR(S) : Wim J. M. Pieters and Emery J. Carlson

It is certified that error appears in the above-identified patent and that said Letters Patent are hereby corrected as shown below:

Col. 2, line 33, "chloride" should read --chlorine--

Col. 5, line 63, "$CuCl_2KCl$" should read --$CuCl_2/KCl$--

Col. 6, line 65, "prgrammer" should read --programmer--

Col. 7, line 17, "cmponents" should read --components--

"  Deacon           "   should read   -- Deacon         --
  based    Perf                          based    Perf
  on HCL   fact                          on HCL   fact
   (8)     (9)                            (8)      (9)

Col. 7, line 68, "Selectiivity" should read --Selectivity--

Col. 8, line 9, "extent" should read --Extent--

Col. 8, line 17, "utliziation" should read --utilization--

Col. 8, line 21, "(Depth/87)2" should read --$(Depth/87)^2$--

Col. 9, line 59, "fun" should read --run--

Col. 9, line 62 through Col. 10, line 1, "assigned cost " change in" should read --assigned <u>cost X change</u> in--

UNITED STATES PATENT AND TRADEMARK OFFICE
CERTIFICATE OF CORRECTION

PATENT NO. : 4,113,655

DATED : September 12, 1978

INVENTOR(S) : Wim J. M. Pieters and Emery J. Carlson

It is certified that error appears in the above-identified patent and that said Letters Patent are hereby corrected as shown below:

Col. 11-12, Table II, Run No. 24, "93.4" under Depth should read --85.0--; "77" under Deacon% should read --93.4--; and --77-- should be inserted under Perf Fact Col. 11, line 44, "KCl/0.88 gm. g. of LiCl," should read --KCl/0.88 gm. of LiCl,--

Col. 11, line 57, "0.67 Kcl," should read --0.67 KCl,--

Col. 12, line 50, "aliqot" should read --aliquot--

Col. 13-14, Table III, Part H, Run 41, "1.77" under HCl should read --31.2--

Col. 13-14, Table III, Explanations of Headings of Results,

Item (2), "$100[CM]/[CH4]_{in} = 100$ X" should read --$100[CM]/[CH_4]_{in} = 100$ X--

Item (3), "$100 \times \{[HCl]_{in} + [HCl]$" should read --$100 \times \{[HCl]_{in} + [HCl]$--

Item (4), "$100 \times \{[HF]_{in} - [HF]$" should read --$100 \times \{[HF]_{in} - [HF]$--

Item (5), "$100 \times \{2[CCl2^F2]_{net} + [CCl_3F]$" should read --$100 \times \{2[CCl_2F_2]_{net} + [CCl_3F]$--

UNITED STATES PATENT AND TRADEMARK OFFICE
CERTIFICATE OF CORRECTION

PATENT NO. : 4,113,655            Page 3 of 3

DATED       : September 12, 1978

INVENTOR(S) : Wim J. M. Pieters and Emery J. Carlson

It is certified that error appears in the above–identified patent and that said Letters Patent are hereby corrected as shown below:

Col. 13, line 40, "mole" should read --mol--; and
"$CuCl_2:CaCl_2.2H_2O$" should --$CuCl_2:CaCl_2 \cdot 2H_2O$--

Col. 13-14, Table IV, "Temperature     Exit Composition " should read
°C    $O_2$    CO --Temperature     Exit Composition --
°C    $O_2$    CO Col. 15, line 7, "copper-calcium" should read --copper:calcium--

Col. 16, line 1, "the precipitate, and" should read --the precipitate; and--

Signed and Sealed this

Sixteenth Day of January 1979

[SEAL]

Attest:

RUTH C. MASON
*Attesting Officer*

DONALD W. BANNER
*Commissioner of Patents and Trademarks*